United States Patent
Lange et al.

(10) Patent No.: US 10,456,349 B2
(45) Date of Patent: Oct. 29, 2019

(54) PRODUCT FOR KERATIN FIBERS, CONTAINING AT LEAST ONE COPOLYMER BASED ON VINYLPYRROLIDONE AND AT LEAST ONE COPOLYMER BASED ON ACRYLATES

(71) Applicant: Henkel AG & Co. KGaA, Duesseldorf (DE)

(72) Inventors: Julia Bibiane Lange, Bad Bramstedt (DE); Anna Puls, Winsen (DE); Cyrielle Martinez, Hamburg (DE); Bernd Richters, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 102 days.

(21) Appl. No.: 15/561,523

(22) PCT Filed: Jan. 26, 2016

(86) PCT No.: PCT/EP2016/051568
§ 371 (c)(1),
(2) Date: Sep. 26, 2017

(87) PCT Pub. No.: WO2016/155901
PCT Pub. Date: Oct. 6, 2016

(65) Prior Publication Data
US 2018/0064627 A1    Mar. 8, 2018

(30) Foreign Application Priority Data

Mar. 31, 2015  (DE) .................. 10 2015 205 759

(51) Int. Cl.
*A61K 8/81* (2006.01)
*A61K 8/41* (2006.01)
*A61Q 5/06* (2006.01)
*A61Q 5/04* (2006.01)

(52) U.S. Cl.
CPC .............. *A61K 8/8182* (2013.01); *A61K 8/41* (2013.01); *A61K 8/8152* (2013.01); *A61K 8/8158* (2013.01); *A61Q 5/04* (2013.01); *A61Q 5/06* (2013.01); *A61K 2800/594* (2013.01)

(58) Field of Classification Search
CPC .. A61K 2800/594; A61K 8/41; A61K 8/8152; A61K 8/8158; A61K 8/8182; A61Q 5/04; A61Q 5/06
See application file for complete search history.

(56) References Cited

U.S. PATENT DOCUMENTS

| 2011/0135589 A1* | 6/2011 | Knappe ................ A61K 8/8182 424/70.12 |
| 2014/0369948 A1 | 12/2014 | Mellen et al. |

FOREIGN PATENT DOCUMENTS

| DE | 102008059480 A1 | 6/2010 | |
| EP | 1502577 | * 2/2005 | .............. A61K 8/73 |
| EP | 1502577 A2 | 2/2005 | |
| WO | WO 2013/072118 | * 5/2013 | |

OTHER PUBLICATIONS

EPO, International Search Report and Written Opinion issued in International Application No. PCT/EP2016/051568, dated Mar. 11, 2016.
Ashland, "Styleze W-20 polymer—A new cationic polymer for a conditioning hold even in high humidity", Brochure, pp. 1-8, 2015, Global Headquarters, Ashland Inc., Covington, KY.
Ashland, "AquaStyle 300 and AquaStyle 300 AF polymers—Delivering strong, durable, humidity-resistant hold with all-day frizz control", Brochure, 2012, Global Headquarters, Ashland Inc., Covington, KY.
International Specialty Products (ISP), Aquastyle 300—"Safety Data Sheet (1907/2006)", SDS Statement, Issue date: Feb. 6, 2012, pp. 1-8, Wayne, NY.
International Specialty Products (ISP), Styleze W-20—"Material Safety Data Sheet", MSDS Statement, Issue date: Jan. 18, 2006, pp. 1-5, Wayne, NY.

* cited by examiner

*Primary Examiner* — Anna R Falkowitz
(74) *Attorney, Agent, or Firm* — Lorenz & Kopf, LLP

(57) ABSTRACT

The disclosure relates to a cosmetic product for temporary shaping keratin fibers, in particular human hair, containing a combination of a copolymer A based on vinylpyrrolidone with copolymer B based on acrylates. Said cosmetic product has a good level of moisture resistance. The disclosure also relates to the use of said cosmetic product and to a method for temporary shaping keratin fibers using said product.

17 Claims, No Drawings

PRODUCT FOR KERATIN FIBERS, CONTAINING AT LEAST ONE COPOLYMER BASED ON VINYLPYRROLIDONE AND AT LEAST ONE COPOLYMER BASED ON ACRYLATES

CROSS-REFERENCE TO RELATED APPLICATION

This application is a U.S. National-Stage entry under 35 U.S.C. § 371 based on International Application No. PCT/EP2016/051568, filed Jan. 26, 2016 which was published under PCT Article 21(2) and which claims priority to German Application No. 10 2015 205 759.3, filed Mar. 31, 2015, which are all hereby incorporated in their entirety by reference.

TECHNICAL FIELD

The present patent application relates to the technical field of temporary shaping of keratin-containing fibers, in particular human hair. The subject matter of the patent application is cosmetic agents containing at least one copolymer A based on vinyl pyrrolidone and at least one copolymer B based on acrylates. In addition the subject matter of the present patent application is the use of these cosmetic agents as well as corresponding application methods.

BACKGROUND

An attractive looking hairstyle is today regarded in general as an indispensable part of a well-groomed appearance. Because of current fashion trends, the hairstyles that are considered to be chic are repeatedly those that, with many types of hair, can be created and/or maintained for a longer period of up to several days only by using hair setting agents. Therefore, hair treatment agents that provide permanent or temporary shaping of hair play an important role. In permanent shaping, the chemical structure of the keratin-containing fibers is modified by oxidation and reduction, but such modifications of the temporary structure do not take place in temporary shaping. Corresponding agents for temporary shaping usually contain synthetic polymers and/or waxes as the hair setting ingredient.

The most important property of an agent for temporary shaping of keratinic fibers, hereinafter also referred to as styling agents, consists of imparting the strongest possible hold to the treated fibers in the shaped form, i.e., a form imposed upon the fibers. If the keratinic fibers are human hair, we also speak of a strong hairstyle hold or a high degree of hold of the styling agent. The hairstyle hold is determined essentially by the type and amount of styling active ingredients used, but there may also be an influence of the additional ingredients of the styling agent as well as the form of application.

In addition to a high degree of hold, styling agents must meet a number of other requirements. These may be subdivided roughly into properties involving the hair, properties involving the respective formulation. e.g., the sprayed aerosol or non-aerosol, and properties relating to the handling of the styling agent, but the properties involving the hair are particularly important. Properties that can be mentioned here include in particular a moisture resistance, a low stickiness and a balanced conditioning effect. Furthermore, a styling agent should be universally applicable for all types of hair and should be mild on hair and skin.

To do justice to the various requirements, a variety of synthetic polymers, which are used as hair setting agents in styling agents have been developed in the state of the art. These polymers can be subdivided into cationic, anionic, nonionic and amphoteric hair setting polymers. When applied to hair, these polymers ideally form a polymer film, which, on the one hand, imparts a strong hold to the hair style, but, on the other hand, is flexible enough not to break under stress. If the polymer film is fragile, then the result is the formation of so-called film flakes and residues, which become detached from the hair with movement and give the impression that the user of the respective styling agent has dandruff The polymer films that can be obtained with the synthetic polymers and polymer combinations known in the state of the art have a satisfactory hold, but the hold thereby achieved for the hairstyle suffers drastically in a humid environment. In a humid environment, however, this deteriorating hold will not meet the user's demand for a uniformly strong, long-term hold regardless of external weather factors. Therefore, there is a need for improving the moisture resistance of polymer films that can be obtained by using polymers and polymer combinations but without a negative influence on the other properties of cosmetic agents mentioned above, in particular styling agents.

BRIEF SUMMARY

A cosmetic agent for temporary shaping of keratinic fibers is provided herein. The cosmetic agent includes in a cosmetically tolerable vehicle a) at least one copolymer A including at least one structural unit of formula (I) and at least one structural unit of formula (II) and at least one structural unit of formula (III):

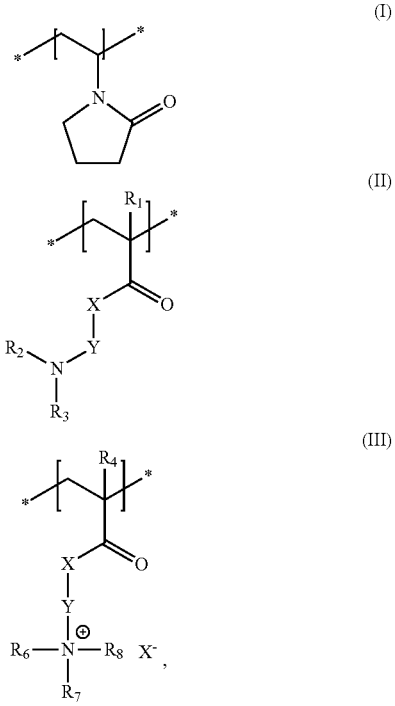

where
$R_1$ and $R_4$ each independently of one another stand for hydrogen or a $C_{1-4}$ alkyl group, X stands for oxygen or an NH group,
Y stands for a $C_{2-10}$ alkyl group,
$R_2$, $R_3$, $R_6$, $R_8$ each independently of one another stand for a $C_{1-8}$ alkyl group,
$R_7$ stands for a linear or branched, saturated or unsaturated $C_{6-30}$ alkyl group and
$X^-$ stands for a physically tolerable anion, in particular chloride.

The cosmetic agent includes further includes b) at least one copolymer B including at least one structural unit of formula (IV) and at least one structural unit of formula (V) and at least one structural unit of formula (VI):

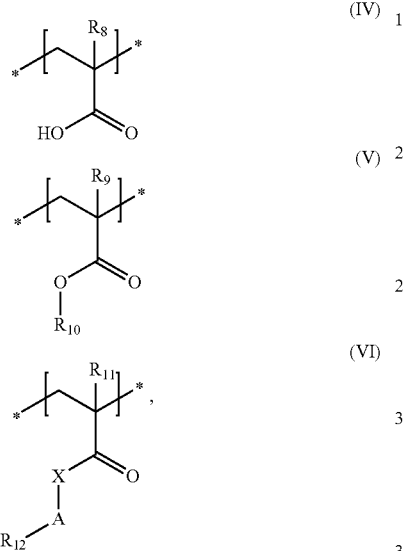

where
$R_8$, $R_9$ and $R_{11}$ each independently of one another, stand for hydrogen or a $C_{1-4}$ alkyl group,
$R_{10}$ stands for a $C_{1-6}$ alkyl group,
X stands for oxygen or an NH group,
A stands for a group $*-(CH_2CH_2O)_n-*$ or for a group $*-(CH_2CHMeO)_m-*$ or for a group $*-(CH_2CH_2O)_n-(CH_2CHMeO)_m-*$ where n and m, each independently of one another, stand for integers from 5 to 35,
$R_{12}$ stands for a linear or branched, saturated or unsaturated $C_{8-30}$ alkyl group.

The cosmetic agent includes further includes c) at least one alkaline compound.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Therefore, the object of the present disclosure was to make available novel polymer combinations which also have an excellent moisture resistance—in particular a resistance to perspiration and water—in addition to having a high long-term hold, a high flexibility and a low stickiness. In addition, these polymer combinations should enable the formulation to be stable and more viscous and permit transparent agents to be used for temporary shaping of keratinic fibers.

It has now surprisingly been found that a combination of a copolymer A based on polyvinyl pyrrolidone in a copolymer B based on acrylates would lead to styling agents, which yield a greater hold and a good flexibility in combination with excellent moisture resistance at the same time. The combination of the polymers surprisingly results in a synergistic effect with respect to moisture resistance, which has been determined with the help of the HHCR test (high humidity curl retention test). The polymer combination as contemplated herein did not have a negative effect on the low stickiness of the cosmetic agents, which is required for pleasant haptic properties. Furthermore, stable viscous and transparent cosmetic agents can be formulated by using this polymer combination.

Another subject matter of the present disclosure is thus a cosmetic agent for temporary shaping of keratinic fibers, containing in a cosmetically tolerable vehicle:

a) at least one copolymer A, comprising at least one structural unit of formula (I) and at least one structural unit of formula (II) and at least one structural unit of formula (III):

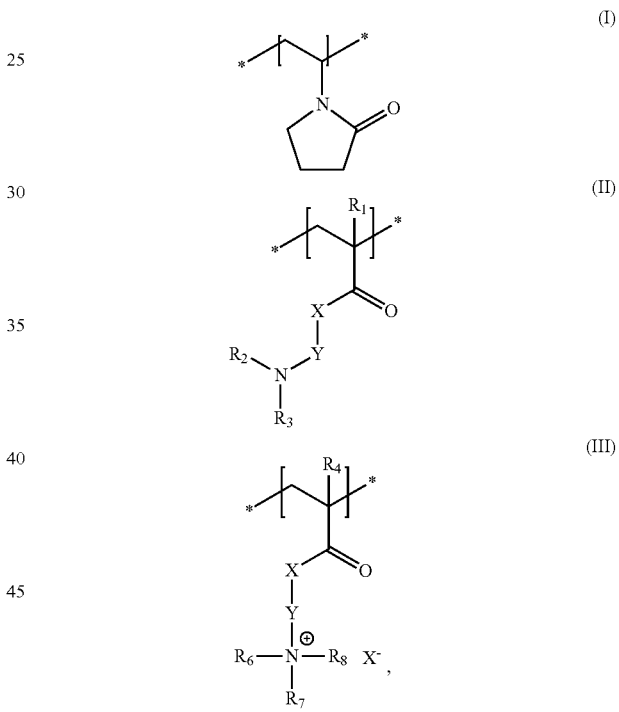

Where
$R_1$ and $R_4$ each independently of one another, stand for hydrogen or a $C_{1-4}$ alkyl group,
X stands for oxygen or an NH group,
Y stands for a $C_{2-10}$ alkyl group,
$R_2$, $R_3$, $R_6$, $R_8$ each independently of one another, stand for a $C_{1-8}$ alkyl group,
$R_7$ stands for a linear or branched, saturated or unsaturated $C_{6-30}$ alkyl group, and
$X^-$ stands for a physically tolerable anion, in particular chloride, b) at least one copolymer B, comprising at least one structural unit of formula (IV) and at least one structural unit of formula (V) and at least one structural unit of formula (VI):

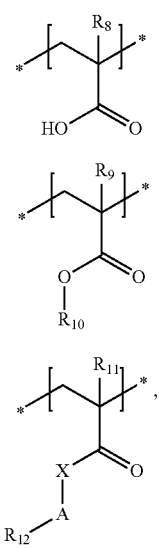

Where
$R_8$, $R_9$ and $R_{11}$ each independently of one another stand for hydrogen or a $C_{1-4}$ alkyl group,
$R_{10}$ stands for a $C_{1-6}$ alkyl group,
X stands for oxygen or an NH group,
A stands for a group *—$(CH_2CH_2O)_n$—* or for a group *—$(CH_2CHMeO)_m$—* or for a group *—$(CH_2CH_2O)_n$—$(CH_2CHMeO)_m$—*, where n and m, each independently of one another, stand for integers from 5 to 35,
$R_{12}$ stands for a linear or branched, saturated or unsaturated $C_{8-30}$ alkyl group, and
c) at least one alkaline compound.

Due to the combination of a copolymer A based on polyvinyl pyrrolidone with a copolymer B based on acrylates, a synergistic effect is achieved with respect to the improved moisture resistance of the cosmetic agents. The agents as contemplated herein therefore ensure a permanent and uniformly high hairstyle hold even under variable external environmental influences. In addition the use of the polymer combination listed above does not have a negative effect on the other product properties such as the stickiness of the products. Furthermore this polymer combination also has no negative effects on the viscosity or the desired transparency of the cosmetic agents.

According to the above formulas and all the following formulas, there is a chemical bond, which is exemplified by the symbol "*" and stands for a free valence of the corresponding fragment of structure. The term free valence is understood here to refer to the number of atomic bonds which emanate from the fragment of structure at the position labeled with the symbol "*". Within the scope of the present disclosure, an atomic bond preferably emanates from the positions of the fragments of structure exemplified by the symbol "*" to other structure fragments.

The term "keratin-containing fibers" is understood in principle to include all types of animal hair, for example, wool, horsehair, angora hair, furs, feathers and products or textiles manufactured from them. However, the keratinic fibers here are preferably human hair.

Within the context of the present disclosure, the term "alkaline compounds" are understood to refer to those compounds which are capable of splitting off hydroxide ions in protic solvents and/or can form salts when combined with acids by neutralization.

Furthermore, the term "fatty acid" as used in the present disclosure is understood to refer to aliphatic carboxylic acids, which comprise branched or unbranched carbon radicals with 4 to 40 carbon atoms. The fatty acids used within the scope of the present disclosure may include both naturally occurring fatty acids as well as synthetically produced fatty acids. In addition the fatty acids may also be mono- or polyunsaturated.

Finally the concept of a "fatty alcohol" within the scope of the present disclosure is understood to refer to aliphatic monovalent primary alcohols which comprise branched or unbranched hydrocarbon radicals with from about 4 to about 40 carbon atoms. The fatty alcohols used within the scope of the disclosure may also be mono- or polyunsaturated.

As the first essential ingredient a), the cosmetic agent as contemplated herein contains at least one copolymer A which contains at least one structural unit of formulas (I) and (II) and (III). The radicals $R_1$ through $R_6$, $R_8$ and Y in the structural units of formulas (I) to (III) may stand for $C_1$-$C_{10}$ alkyl groups. Examples of such groups include methyl, ethyl, propyl, isopropyl, hydroxypropyl, butyl, sec-butyl, isobutyl, tert-butyl, hydroxybutyl, pentyl, hexyl, heptyl, octyl, nonyl and dodecyl groups. In addition the $R_7$ radical in the structural unit of formula (III) may stand for a $C_6$-$C_{30}$ alkyl group. Such groups include for example caprylic, capric, lauryl, myristyl, cetyl, stearyl, arachidyl, behenyl, oleyl and ceryl groups.

Within the scope of the present disclosure, it is preferably for copolymer A to contain from about 55 to about 68% by weight, preferably from about 62 to about 68% by weight structural units of formula (I), from about 5 to about 15% by weight, preferably from about 7 to about 9% by weight structural units of formula (II) and from about 25 to about 35% by weight, preferably from about 27 to about 31% by weight structural units of formula (III), each based on the total weight of copolymer A. Copolymers A having the monomer distribution indicated above when combined with the crosslinked specific copolymer B result in a particularly high moisture resistance of the cosmetic agents as contemplated herein.

Within the scope of the present disclosure it is advantageous if the radicals $R_1$ and $R_4$ in the structural units of formulas (I) and (II) stand for certain groups. It is also preferable for the radicals $R_1$ and $R_4$ each independently of one another to stand for a hydrogen atom or a methyl group in the structural units of formulas (II) and (III).

In addition, it is preferable as contemplated herein if the radicals $R_2$, $R_3$, $R_6$ and $R_8$, each independently of one another, stand for a methyl group in the structural units of formula (II) and (III).

In addition, it has proven advantageous within the scope of the present disclosure if X and Y in the structural units of formulas (II) and (III) stand for certain groups. It is therefore preferred as contemplated herein if X in the structural units of formulas (II) and (III) stands for an NH group and Y stands for a $C_{2-8}$ alkyl group, preferably a $C_{2-6}$ alkyl group, in particular a $C_3$ alkyl group.

It is also preferable if the radical $R_7$ in the structural unit of formula (III) stands for a long-chain alkyl group. Therefore the radical $R_7$ in the structural unit of formula (III) preferably stands for a linear or branched, saturated or unsaturated $C_{8-25}$ alkyl group, preferably a linear or branched, saturated or unsaturated $C_{8-20}$ alkyl group, preferably a linear or branched, saturated or unsaturated $C_{8-15}$ alkyl group, in particular a linear or branched, saturated or unsaturated $C_{8-12}$ alkyl group.

Particularly good results with respect to the moisture resistance of the cosmetic agents as contemplated herein and thus the hold under various external weather influences are obtained when the copolymer A contains at least on structural unit of formula (I) and at last one structural unit of formula (IIa) and at least one structural unit of formula (IIIa):

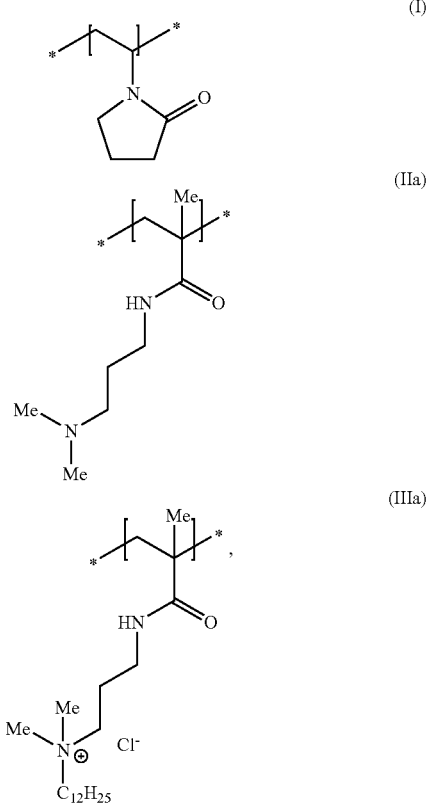

The copolymer A especially preferably consists of the aforementioned structural units of formulas (I), (IIa) and (IIIa). Use of such copolymers A in combination with the at least one specific copolymer B results in a synergistic effect with respect to the moisture resistance in comparison with the moisture resistance obtained with the individual copolymers.

A most especially preferred copolymer A within the scope of this embodiment is a polymer having the INCI designation polyquaternium 55 (CAS number 306769-73-3). This polymer is a terpolymer of vinyl pyrrolidone, dimethylaminopropyl methacrylamide and (meth)acryloylaminopropyl-lauryldimethyl ammonium chloride. Such polymers are distributed by the company ISP under the brand names Styleze W20, for example.

Preferred cosmetic agents as contemplated herein contain the at least one copolymer A in a total amount of from about 0.01 to about 5.0% by weight, preferably from about 0.05 to about 4.0% by weight, preferably from about 0.1 to about 3.0% by weight, in particular from about 0.2 to about 1.5% by weight, based on the total weight of the cosmetic agent. Use of these amounts of copolymer A results in the aforementioned synergistic effect with respect to the moisture resistance in combination with the specific copolymer B. In addition, these amounts also ensure an excellent hold with the cosmetic agents as contemplated herein, in addition to the excellent moisture resistance. Furthermore, when using these amounts, a stable viscosity of these agents and a sufficient transparency of these agents are ensured.

As the second essential ingredient b), the cosmetic agent as contemplated herein contains at least one copolymer B which contains at least one structural unit of formulas (IV), (V) and (VI). The radicals $R_8$ to $R_{11}$ in the structural units of formulas (IV) through (VI) may stand for $C_1$-$C_6$ alkyl groups.

Examples of such groups include methyl, ethyl, propyl, isopropyl, hydroxypropyl, butyl, sec-butyl, isobutyl, tert-butyl, hydroxybutyl, pentyl and hexyl groups. In addition, the $R_{12}$ radical in the structural unit of formula (VI) may stand for a $C_6$-$C_{30}$ alkyl group. Such groups include, for example, caprylic, capric, lauryl, myristyl, cetyl, stearyl, arachidyl, behenyl, oleyl and ceryl groups.

The radicals $R_8$, $R_9$ and $R_{11}$, independently of one another, in the structural units of formula (IV) and (V) and (VI) each preferably stand for hydrogen or a methyl group.

In addition, it is preferable as contemplated herein for X in the structural unit of formula (VI) to stand for an oxygen atom, and for A to stand for a group *—$(CH_2CH_2O)_n$—*, where n stands for integers from 10 to 30, in particular from 20 to 30.

Within the scope of the present disclosure, it is also preferable if the radical $R_{12}$ in the structural unit of formula (VI) stands for a linear or branched, saturated or unsaturated $C_{10-28}$ alkyl group, preferably a linear or branched, saturated or unsaturated $C_{12-26}$ alkyl group, especially a linear or branched, saturated or unsaturated $C_{16-24}$ alkyl group, in particular a linear or branched, saturated or unsaturated $C_{20-24}$ alkyl group.

Within the scope of the present disclosure, it is therefore especially preferable if the copolymer B contains at least one structural unit of formula (IVa) and at least one structural unit of formula (IVb) and at least one structural unit of formula (Va) and at least one structural unit of formula (Vb) and at least one structural unit of formula (VIa):

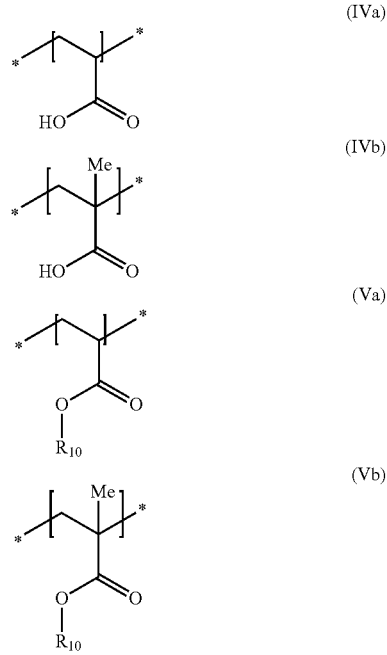

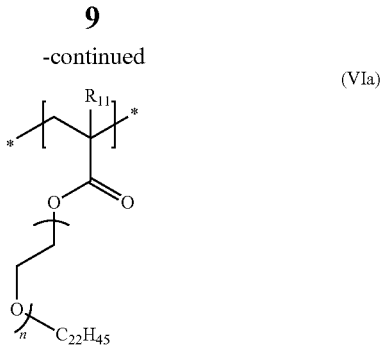

where
R$_{10}$ stands for a C$_{1-6}$ alkyl group,
R$_{11}$ stands for hydrogen or a methyl group, and
n stands for an integer from 22 to 26.

The copolymer B especially preferably consists of the aforementioned structural units of formulas (IVa) and/or (IVb) and/or (Va) and/or (Vb) and (VIa). Use of such copolymers B in conjunction with copolymer A results in a significant increase in moisture resistance.

A polymer that is especially preferably used as copolymer B is a polymer with the INCI designation acrylates/beheneth-25 methacrylate copolymer, which is available commercially from the company Rohm & Haas under the designation Aculyn 28, has a solids content of approx. 19.0 to 21.0% by weight and a pH of from about 3.5 to about 4.0.

Preferred cosmetic agents as contemplated herein contain the at least one copolymer B in a total amount of from about 0.01 to about 5.0% by weight, preferably from about 0.05 to about 4.0% by weight, especially from about 0.1 to about 3.0% by weight, in particular from about 0.2 to about 1.5% by weight, based on the total weight of the cosmetic agent. Use of the aforementioned amounts of copolymer B in combination with copolymer A results in a synergistic effect with respect to the moisture resistance of the cosmetic agents. In addition, these amounts assure a good hold of the cosmetic agents and an adequate flexibility. Furthermore, when the aforementioned amounts are used, there are no adverse effects on stickiness, viscosity or transparency of the cosmetic agents as contemplated herein.

It has proven advantageous for the cosmetic properties of the agents as contemplated herein if the cosmetic agent has a weight ratio of the total amount of the at least one copolymer A to the total amount of the at least one copolymer B of from about 25:1 to about 1:20.

Copolymers A and/or B are used in a neutralized or partially neutralized form in the cosmetic agents as contemplated herein. For neutralization, these agents therefore contain at least one alkaline compound c).

Within the scope of the present disclosure, it has proven advantageous to use in particular primary amines with a C$_2$-C$_6$ alkyl base body, which has at least one hydroxyl group, as the alkanolamine. Therefore, the alkaline compound c) is preferably selected from the group of 2-aminoethan-1-ol (monoethanolamine), tris(2-hydroxyethyl)amine (triethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 2-amino-2-methylpropan-1-ol, 1-amino-2-methylpropan-2-ol, 3-aminopropane-1,2-diol, 2-amino-2-methylpropane-1,3-diol, in particular 2-amino-2-methylpropan-1-ol. Especially preferred cosmetic agents as contemplated herein therefore contain 2-amino-2-methylpropanol as the alkaline compound c).

The alkaline compound c) is preferably used in an amount not exceeding the amount required for neutralization of copolymers A and B. The amount of alkaline compound used in the compositions as contemplated herein is preferably from about 80% to about 100%, especially preferably from about 90% to about 100% and in particular from about 95% to about 100% of the amount required for complete neutralization of copolymers A and/or B. In a preferred embodiment, the alkaline compound c) is therefore present in a total amount of from about 0.05% to about 7.0% by weight, preferably from about 0.1% to about 5.0% by weight, especially from about 0.1% to about 4.0% by weight, in particular from about 0.1% to about 3.0% by weight, based on the total amount of the cosmetic agent.

The cosmetic agents as contemplated herein contain copolymers A and B, the alkaline compound c) and optionally additional ingredients in a cosmetically tolerable vehicle.

Preferred cosmetically tolerable vehicles include aqueous, alcoholic or aqueous-alcoholic media, preferably with at least about 10% by weight water, based on the total weight of the cosmetic agent.

The cosmetically tolerable vehicle especially preferably contains water, in particular in an amount such that the cosmetic agent contains, calculated based on the total weight of the cosmetic agent, at least about 10% by weight, preferably at least about 20% by weight, in particular at least about 40% by weight water. Most especially preferred cosmetic agents have, based on their total weight, a water content of from about 50% to about 95% by weight, preferably from about 60% to about 90% by weight, in particular from about 65% to about 85% by weight.

In particular the lower alcohols with 1 to 4 carbon atoms, for example, ethanol and isopropanol that are generally used for cosmetic purposes may be used as the alcohols.

Examples of water-soluble solvents as co-solvents include glycerin and/or ethylene glycol and/or 1,2-propylene glycol, which may be used in an amount of from about 0 to about 30% by weight, based on the total weight of the cosmetic agent.

The long-term stability of the cosmetic agent as contemplated herein can be increased further if the agent contains at least one additional film-forming polymer and/or hair setting polymer which is/are different from copolymer A and copolymer B. However, it may also be preferable to use exclusively the copolymer A described above and the copolymer B described above as the film-forming and/or hair setting polymers.

Film-forming and/or hairstyling polymers contribute to the hold of the shape imposed on the collection of fibers, e.g., the overall hairstyle. Film-forming may also involve just points and may connect only a few fibers to one another. Film-forming and/or hair setting polymers are understood to be polymers which leave a continuous film on skin, hair or nails when dry. Such film-forming substances may be used in a wide variety of cosmetic products, such as, for example, face masks, makeup, hair setting products, hair sprays, hair gels, hair waxes, intensive hair treatments, shampoos or nail polish. Polymers having adequate solubility in water or water/alcohol mixtures are preferred in particular, so that they will be present in completely dissolved form in the cosmetic agents as contemplated herein. The film-forming polymers may be of synthetic or natural origin. Film-forming polymers are also understood to be polymers which, when used in an amount of from about 0.01 to about 20% by weight aqueous, alcoholic or aqueous-alcoholic solution, are capable of depositing a transparent polymer film on hair.

In this context, it may be provided in particular as contemplated herein that the additional film-forming and/or hair setting polymer is selected from copolymers of polyvinyl pyrrolidone with vinyl acetate. Within the scope of the present disclosure, in particular polyvinyl pyrrolidone/vinyl acetate copolymers are available with a molar ratio of polyvinyl pyrrolidone to vinyl acetate of about 70:30, about 60:40, about 50:50 or about 30:70. Such PVP/VA copolymers with a molar ratio of polyvinyl pyrrolidone to vinyl acetate of 70:30 are available from the Ashland Co., for example, under the brand names PVP/VA E-735, PVP/VA I-735 and PVP/VA W-735 as 50% dispersions in ethanol, isopropanol and/or water. PVP/VA copolymers with a 60:40 molar ratio of polyvinyl pyrrolidone to vinyl acetate are distributed by the Ashland Co., for example, under the brand names PVP/VA E-635 and PVP/VA W-635 as 50% dispersions in ethanol, isopropanol and/or water. PVP/VA copolymers with a molar ratio of polyvinyl pyrrolidone to vinyl acetate of 50:50 are available as 50% dispersions in ethanol or isopropanol from the Ashland Co. under the brand names PVP/VA E-535 and PVP/VA I-535. A PVP/VA copolymer with a molar ratio of polyvinyl pyrrolidone to vinyl acetate of 30:70 is distributed by the Ashland Co. under the brand name PVP/VA I-335 as a 50% dispersion in isopropanol.

In addition to the copolymers of polyvinyl pyrrolidone with vinyl acetate, the cosmetic agents as contemplated herein may contain in this context additional film-forming and/or hair setting polymers selected from the group of polymers of vinyl pyrrolidone, copolymers of vinyl pyrrolidone with vinyl imidazole and/or acrylamide and/or (meth)acrylamide, copolymers of isobutene as well as blends thereof. These polymers are also different from copolymer A and the crosslinked polyurethane-vinyl polymer B.

These film-forming and/or hair setting polymers are in turn preferably selected from at least one polymer of the group formed by
polyvinylpyrrolidone,
copolymers of N-vinylpyrrolidone and N-vinylimidazole and (meth)acrylamide,
copolymers of N-vinylpyrrolidone and N-vinylimidazole and acrylamide,
copolymers of N-vinylpyrrolidone with N,N-di-$C_1$-$C_4$-alkylamino-$C_2$-$C_4$-alkylacrylamide,
copolymers of N-vinylpyrrolidone with N,N-di-$C_1$-$C_4$-alkylamino-$C_2$-$C_4$-alkylacrylamide,
copolymers of isobutene.

Suitable polyvinyl pyrrolidones include, for example, commercial products such as Luviskol® K 90 or Luviskol® K 85 from BASF SE. Suitable polyvinyl alcohols are distributed, for example, by DuPont under the brand name Elvanol® or by Air Products Co. under the brand name Vinol® 523/540.

The additional film-forming and/or hair setting polymers may preferably be present in the cosmetic agents as contemplated herein in a total of from about 0.1% by weight to about 12.0% by weight, preferably from about 0.2% by weight to about 10.0% by weight, in particular from about 0.5% by weight to about 8.0% by weight, each based on the total weight of the cosmetic agent.

According to a particularly preferred embodiment of the present disclosure, the cosmetic agent is in the form of a gel. The term "gel" within the scope of the present disclosure is understood to be a dimensionally stable and easily shapeable system of two components, wherein one component, embodied in the form of a thickener and/or gel-forming agent, forms a three-dimensional spatial network with the second component incorporated into its cavities and/or pores in the form of a liquid, in particular water.

To achieve a gelatinous consistency, additional component(s), which act as thickeners or gel-forming agents and is/are different from copolymer A and the crosslinking polyurethane vinyl copolymer B, are used. The total amount of these thickeners in the total weight of the cosmetic agent is from about 0.02% to about 3% by weight for example, preferably from about 0.05% to about 1.5% by weight, in particular from about 0.2% to about 0.8% by weight.

Examples include acrylamide/ammonium acrylate copolymer, acrylamides/DMAPA acrylates/methoxy PEG methacrylate copolymer, acrylamidopropyltrimonium chloride/acrylamide copolymer, acrylamidopropyltrimonium chloride/acrylates copolymer, acrylates/acetoacetoxyethyl methacrylate copolymer, acrylates/acrylamide copolymer, acrylates/ammonium methacrylate copolymer, acrylates/t-butylacrylamide copolymer, acrylates/$C_{1-2}$ succinates/hydroxyacrylates copolymer, acrylates/lauryl acrylate/stearyl acrylate/ethylamine oxide methacrylate copolymer, acrylates/octylacrylamide copolymer, acrylates/octylacrylamide/diphenyl amodimethicone copolymer, acrylates/stearyl acrylate/ethylamine oxide methacrylate copolymer, acrylates/VA copolymer, acrylates/VP copolymer, adipic acid/diethylenetriamine copolymer, adipic acid/dim ethylaminohydroxypropyl diethylenetriamine copolymer, adipic acid/epoxypropyldiethylenetriamine copolymer, adipic acid/isophthalic acid/neopentyl glycol/trimethylolpropane copolymer, allyl stearate/VA copolymer, aminoethyl acrylate phosphate/acrylates copolymer, aminoethylpropanediol acrylates/acrylamide copolymer, aminoethylpropanediol-AMPD acrylates/diacetone acrylamide copolymer, ammonium VA/acrylates copolymer, AMPD acrylates/diacetone acrylamide copolymer, AMP acrylates/allyl methacrylate copolymer, AMP acrylates/$C_{1-18}$ alkyl acrylates/$C_{1-8}$ alkyl acrylamide copolymer, AMP acrylates/diacetone acrylamide copolymer, AMP acrylates/dimethylaminoethyl methacrylate copolymer, bacillus/rice bran extract/soybean extract ferment filtrate, bis-butyloxyamodimethicone/PEG-60 copolymer, butyl acrylate/ethyl hexyl methacrylate copolymer, butyl acrylate/hydroxypropyl dimethicone acrylate copolymer, butyl ester of ethylene/MA copolymer, butyl ester of PVM/MA copolymer, calcium/sodium PVM/MA copolymer, cornstarch/acrylamide/sodium acrylate copolymer, diethylene glycol amine/epichlorohydrin/piperazine copolymer, dimethicone crosspolymer, diphenyl amodimethicone, ethyl ester of PVM/MA copolymer, hydrolyzed wheat protein/PVP crosspolymer, isobutylene/ethyl maleimide/hydroxyethylmaleimide copolymer, isobutylene/MA copolymer, isobutyl methacrylate/bis-hydroxypropyl dimethicone acrylate copolymer, isopropyl ester of PVM/MA copolymer, lauryl acrylate crosspolymer, lauryl methacrylate/glycol dimethacrylate crosspolymer, MEA-sulfite, methacrylic acid/sodium acrylamidomethyl propane sulfonate copolymer, methacryloyl ethyl betaine/acrylates copolymer, PEG/PPG-25/25 dimethicone/acrylates copolymer, PEG-8/SMDI copolymer, polyacrylamide, polyacrylate-6, poly-beta-alanine/glutaric acid crosspolymer, polybutylene terephthalate, polyester-1, polymethyl acrylate, polyethylene terephthalate, polymethacryloylethyl b etaine, polypentaerythrityl terephthalate, polyperfluoroperhydrophenanthrene, polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-22, polyquaternium-24, polyquaternium-27, polyquaternium-28, polyquaternium-29, polyquaternium-30, polyquaternium-31, polyquaternium-32, polyquaternium-33, polyquaternium-34, polyquaternium-35, polyquaternium-36, polyquaternium-37, polyquaternium-39, polyquaternium-45, polyquaternium-46, polyquaternium-47, polyquaternium-48, polyquaternium-49, polyquaternium-50, polyquaternium-55, polyquaternium-56, polysilicone-9, polyurethane-1, polyurethane-6, polyurethane-10, polyvinyl acetate, polyvinyl butyral, polyvinyl caprolactam, polyvinyl formamide, polyvinyl imidazolinium acetate, polyvinyl methyl ether, potassium butyl ester of PVM/MA copolymer, potassium ethyl ester of PVM/MA copolymer, PPG-70 polyglyceryl-10 ether, PPG-12/SMDI copolymer, PPG-51/SMDI copolymer, PPG-10 sorbitol, PVM/MA copolymer, PVP/VA/itaconic acid copolymer, PVP/VA/vinyl propionate copolymer, rhizobian gum, rosin acrylate, shellac, sodium butyl ester of PVM/MA copolymer, sodium ethyl ester of PVM/MA copolymer, sodium polyacrylate, sterculia urens gum, terephthalic acid/isophthalic acid/sodium isophthalic acid sulfonate/glycol copolymer, trimethylolpropane triacrylate, trimethylsiloxy silyl carbamoyl pullulan, VA/crotonates copolymer, VA/crotonates/methacryloxybenzophenone-1 copolymer, VA/crotonates/vinyl neodecanoate copolymer, VA/crotonates/vinyl propionate copolymer, VA/DBM copolymer, VA/vinyl butyl benzoate/crotonates copolymer, vinyl amine/vinyl alcohol copolymer, vinyl caprolactam/VP/dimethylaminoethyl methacrylate copolymer, VP/acrylates/lauryl methacrylate copolymer, VP/dimethylaminoethyl methacrylate copolymer, VP/DMAPA acrylates copolymer, VP/hexadecene copolymer, VP/vinyl caprolactam/DMAPA acrylates copolymer, yeast palmitate and styrene/VP copolymer.

The thickener or gel-forming agent is preferably present in a total amount of from about 0.02 to about 3% by weight, preferably from about 0.05 to about 1.5% by weight, in particular from about 0.2 to about 0.8% by weight, based on the total weight of the cosmetic agent.

A particularly preferred thickener for use within the scope of the present disclosure is a homopolyacrylic acid (INCI: carbomer), which is available commercially under the brand name Carbopol® in various forms.

Especially preferred embodiments (A)-(H) of the cosmetic agent as contemplated herein are listed below:
(A):
Cosmetic agent for temporary shaping of keratinic fibers containing in a cosmetically tolerable vehicle—based on its total weight:
a) from about 0.5 to about 10% by weight of at least one of a copolymer A described above,
b) from about 0.1 to about 8.0% by weight of at least one copolymer B described above,
c) from about 0.05 to about 7.0% by weight of at least one of an alkaline compound c) described above,
d) from about 0 to about 10% by weight of at least one of a film-forming and/or hair setting polymer that is described above but is different from copolymer A and copolymer B and
e) from about 0 to about 3% by weight of at least one of a thickener or gel-forming agent described above.
(B):
Cosmetic agent for temporary shaping of keratinic fibers containing in a cosmetically tolerable vehicle, based on its total weight:
a) from about 0.5 to about 10% by weight, preferably from about 1.0 to about 8.0% by weight, especially from about 1.0 to about 6.0% by weight, in particular from about 1.0 to about 5.0% by weight of at least one copolymer A comprising at least one structural unit of formula (I) and at least one structural unit of formula (II) and at least one structural unit of formula (III):

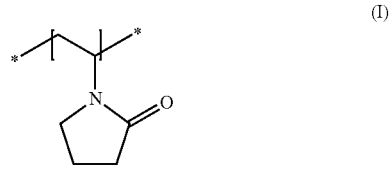

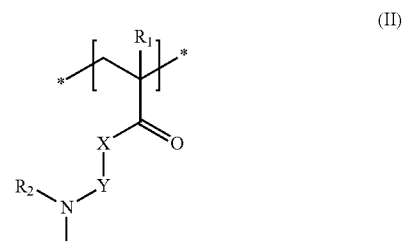

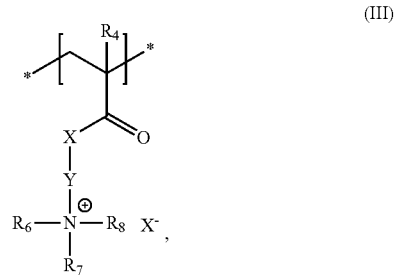

where $R_1$ and $R_4$ each independently of one another stand for hydrogen or a $C_{1-4}$ alkyl group, X stands for oxygen or an NH group, Y stands for a $C_{2-10}$ alkyl group, $R_2$, $R_3$, $R_6$, $R_8$ each independently of one another stand for a $C_{1-8}$ alkyl group, $R_7$ stands for a linear or branched, saturated or unsaturated $C_{6-30}$ alkyl group and $X^-$ stands for a physically tolerable anion, in particular chloride, b) from about 0.1 to about 8.0% by weight, preferably from about 0.2 to about 6.0% by weight, especially from about 0.4 to about 5.0% by weight, more preferably from about 0.8 to about 4.0% by weight, in particular from about 1.2 to about 3.2% by weight of at least one copolymer B comprising at least one structural unit of formula (IV) and at one least structural unit of formula (V) and at least one structural unit of formula (VI):

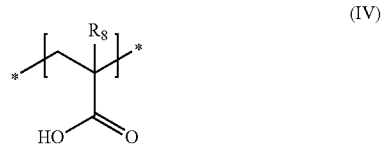

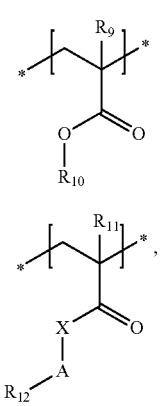 (V)

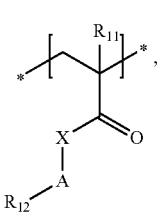 (VI)

where
$R_8$, $R_9$ and $R_{11}$ each independently of one another stand for hydrogen or a $C_{1-4}$ alkyl group,
$R_{10}$ stands for a $C_{1-6}$ alkyl group,
X stands for oxygen or an NH group,
A stands for a group *—$(CH_2CH_2O)_n$—* or for a group *—$(CH_2CHMeO)_m$—* or for a group *—$(CH_2CH_2O)_n$—$(CH_2CHMeO)_m$—*, where n and m each independently of one another stand for integers from 5 to 35,
$R_{12}$ stands for a linear or branched, saturated or unsaturated $C_{8-30}$ alkyl group,
c) from about 0.05 to about 7.0% by weight, preferably from about 0.1 to about 5.0% by weight, especially from about 0.1 to about 4.0% by weight, in particular from about 0.1 to about 3.0% by weight of at least one alkaline compound c) from the group of 2-aminoethan-1-ol (monoethanolamine), tris(2-hydroxyethyl)amine (triethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 2-amino-2-methylpropan-1-ol, 1-amino-2-methylpropan-2-ol, 3-aminopropane-1,2-diol, 2-amino-2-methylpropane-1,3-diol, in particular 2-amino-2-methylpropan-1-ol,
d) from 0 to about 10% by weight, preferably from about 2.0 to about 8.5% by weight, in particular from about 3.0 to about 7.0% by weight of at least one vinyl pyrrolidone polymer and/or vinyl pyrrolidone/vinyl acetate copolymer, and
e) from about 0 to about 3% by weight, preferably from about 0.05 to about 1.5% by weight, in particular from about 0.2 to about 0.8% by weight of a homopolyacrylic acid. (C):
Cosmetic agent for temporary shaping of keratinic fibers containing in a cosmetically tolerable vehicle, based on its total weight:
a) from about 1.0 to about 6% by weight of at least one copolymer A comprising at least one structural unit of formula (I) and at least one structural unit of formula (II) and at least one structural unit of formula (III):

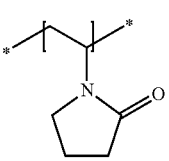 (I)

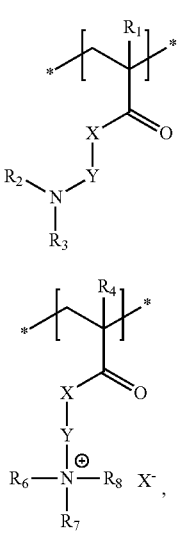 (II)

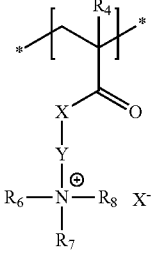 (III)

where
$R_1$ and $R_4$ each independently of one another, stand for hydrogen or a $C_{1-4}$ alkyl group,
X stands for oxygen or an NH group,
Y stands for a $C_{2-10}$ alkyl group,
$R_2$, $R_3$, $R_6$, $R_8$ each independently of one another, stand for a $C_{1-8}$ alkyl group,
$R_7$ stands for a linear or branched, saturated or unsaturated $C_{6-30}$ alkyl group and
$X^-$ stands for a physically tolerable anion, in particular chloride,
b) preferably from about 0.8 to about 4.0% by weight of at least one copolymer B, comprising at least one structural unit of formula (IV) and at one least structural unit of formula (V) and at least one structural unit of formula (VI):

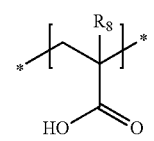 (IV)

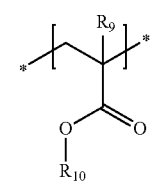 (V)

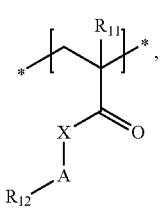 (VI)

where
$R_8$, $R_9$ and $R_{11}$ each independently of one another, stand for hydrogen or a $C_{1-4}$ alkyl group,
$R_{10}$ stands for a $C_{1-6}$ alkyl group, X stands for oxygen or an NH group,
A stands for a group *—$(CH_2CH_2O)_n$—* or for a group *—$(CH_2CHMeO)_m$—* or for a group *—$(CH_2CH_2O)_n$—$(CH_2CHMeO)_m$—* where n and m each independently of one another, stand for integers from 5 to 35,
$R_{12}$ stands for a linear or branched, saturated or unsaturated $C_{8-30}$ alkyl group,
c) from about 0.1 to about 4.0% by weight of at least one alkaline compound c) from the group of 2-aminoethan-1-ol (monoethanolamine), tris(2-hydroxyethyl)amine (triethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 2-amino-2-methylpropan-1-ol, 1-amino-2-methylpropan-2-ol, 3-aminopropane-1,2-diol, 2-amino-2-methylpropane-1,3-diol, in particular 2-amino-2-methylpropan-1-ol,
d) 0 to about 8.5% by weight of at least one vinyl pyrrolidone polymer and/or vinyl pyrrolidone/vinyl acetate copolymer and
e) 0 to about 1.5% by weight of a homopolyacrylic acid.
(D):
Cosmetic agent for temporary shaping of keratinic fibers containing in a cosmetically tolerable vehicle, based on its total weight:
a) from about 1.0 to about 5.0% by weight of at least one copolymer A comprising at least one structural unit of formula (I) and at least one structural unit of formula (II) and at least one structural unit of formula (III):

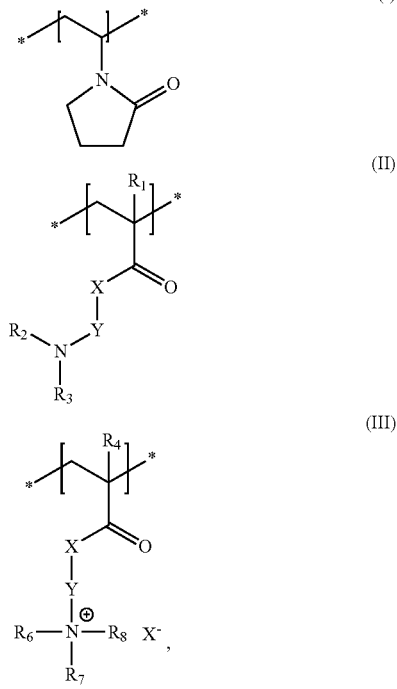

where
$R_1$ and $R_4$ each independently of one another, stand for hydrogen or a $C_{1-4}$ alkyl group,
X stands for oxygen or an NH group,
Y stands for a $C_{2-10}$ alkyl group,
$R_2$, $R_3$, $R_6$, $R_8$ each independently of one another, stand for a $C_{1-8}$ alkyl group,
$R_7$ stands for a linear or branched, saturated or unsaturated $C_{6-30}$ alkyl group, and
$X^-$ stands for a physically tolerable anion, in particular chloride,
b) from about 1.2 to about 3.2% by weight of at least one copolymer B, comprising at least one structural unit of formula (IV) and at one least structural unit of formula (V) and at least one structural unit of formula (VI):

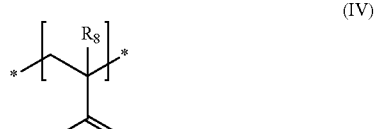

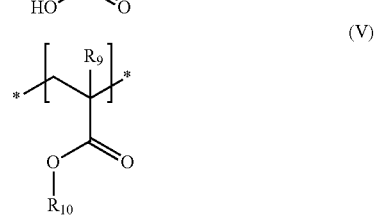

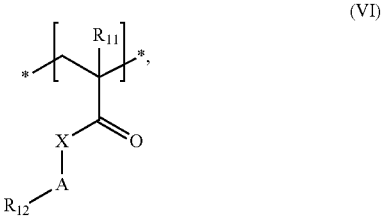

where
$R_8$, $R_9$ and $R_{11}$ each independently of one another, stand for hydrogen or a $C_{1-4}$ alkyl group,
$R_{10}$ stands for a $C_{1-6}$ alkyl group,
X stands for oxygen or an NH group,
A stands for a group *—$(CH_2CH_2O)_n$—* or for a group *—$(CH_2CHMeO)_m$—* or for a group *—$(CH_2CH_2O)_n$—$(CH_2CHMeO)_m$—*, where n and m, each independently of one another, stand for integers from 5 to 35,
$R_{12}$ stands for a linear or branched, saturated or unsaturated $C_{8-30}$ alkyl group,
c) from about 0.1 to about 4% by weight of at least one alkaline compound c) from the group of 2-aminoethan-1-ol (monoethanolamine), tris(2-hydroxyethyl)amine (triethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 2-amino-2-methylpropan-1-ol, 1-amino-2-methylpropan-2-ol, 3-aminopropane-1,2-diol, 2-amino-2-methylpropane-1,3-diol, in particular 2-amino-2-methylpropan-1-ol,
d) 0 to about 7.0% by weight of at least one vinyl pyrrolidone polymer and/or vinyl pyrrolidone/vinyl acetate copolymer and
e) 0 to about 0.8% by weight of a homopolyacrylic acid.
(E):
Cosmetic agent for temporary shaping of keratinic fibers containing in a cosmetically tolerable vehicle, based on its total weight:
a) from about 0.5 to about 10% by weight, preferably from about 1.0 to about 8.0% by weight, especially from about 1.0 to about 6.0% by weight, in particular from about 1.0 to about 5.0% by weight of at least one copolymer A, comprising at least one structural unit of formula (I) and at least one structural unit of formula (IIa) and at least one structural unit of formula (IIIa):

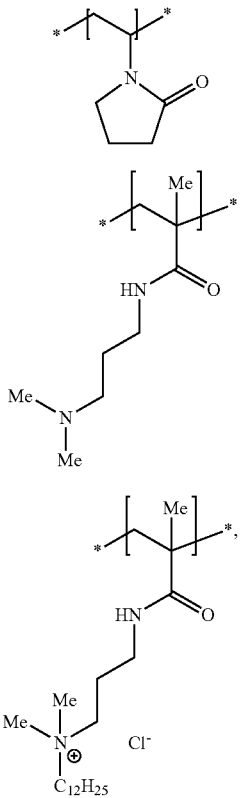

b) from about 0.1 to about 8.0% by weight, preferably from about 0.2 to about 6.0% by weight, especially from about 0.4 to about 5.0% by weight, more preferably from about 0.8 to about 4.0% by weight, in particular from about 1.2 to about 3.2% by weight of at least one copolymer B, comprising at least one structural unit of formula (IVa) and at one least structural unit of formula (IVb) and at least one structural unit of formula (Va) and at least one structural unit of formula (Vb) and at least one structural unit of formula (VIa):

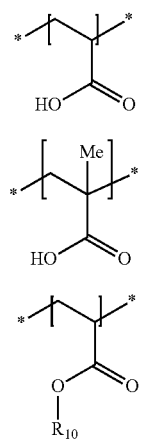

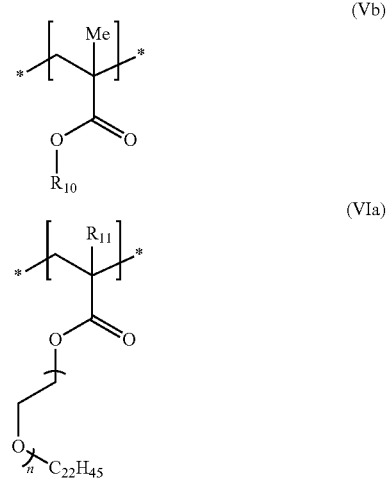

where
$R_{10}$ stands for a $C_{1-6}$ alkyl group,
$R_{11}$ stands for hydrogen or a methyl group, and
n stands for integers from about 22 to about 26,
c) from about 0.05 to about 7.0% by weight, preferably from about 0.1 to about 5.0% by weight, especially from about 0.1 to about 4.0% by weight, in particular from about 0.1 to about 3.0% by weight of at least one alkaline compound c) in the form of 2-amino-2-methylpropan-1-ol,
d) 0 to about 10% by weight, preferably from about 2.0 to about 8.5% by weight, in particular from about 3.0 to about 7.0% by weight of at least one vinyl pyrrolidone polymer and/or vinyl pyrrolidone/vinyl acetate copolymer and
e) 0 to about 3% by weight, preferably from about 0.05 to about 1.5% by weight, in particular from about 0.2 to about 0.8% by weight of a homopolyacrylic acid.
(F):
Cosmetic agent for temporary shaping of keratinic fibers, containing in a cosmetically tolerable vehicle, based on its total weight:
a) from about 1.0 to about 5.0% by weight of at least one copolymer A, comprising at least one structural unit of formula (I) and at least one structural unit of formula (IIa) and at least one structural unit of formula (IIIa):

-continued (IIIa)
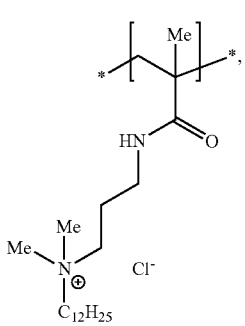

b) from about 1.2 to about 3.2% by weight of at least one copolymer B, comprising at least one structural unit of formula (IVa) and at one least structural unit of formula (IVb) and at least one structural unit of formula (Va) and at least one structural unit of formula (Vb) and at least one structural unit of formula (VIa):

(IVa)
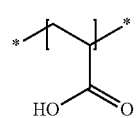

(IVb)
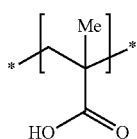

(Va)
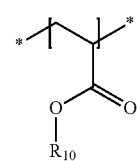

(Vb)
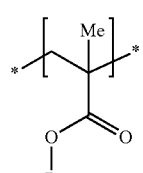

(VIa)
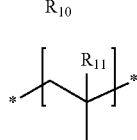
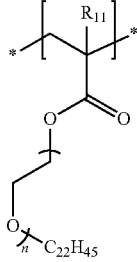

where
$R_{10}$ stands for a $C_{1-6}$ alkyl group,
$R_{11}$ stands for hydrogen or a methyl group, and
n stands for integers from about 22 to about 26,
c) from about 0.1 to about 4.0% by weight of at least one alkaline compound c) in the form of 2-amino-2-methylpropan-1-ol,
d) 0 to about 8.5% by weight of at least one vinyl pyrrolidone polymer and/or vinyl pyrrolidone/vinyl acetate copolymer and
e) 0 to about 1.5% by weight of a homopolyacrylic acid.

(G):

Cosmetic agent for temporary shaping of keratinic fibers containing in a cosmetically tolerable vehicle, based on its total weight:

a) from about 1.0 to about 5.0% by weight of at least one copolymer A, consisting of structural units of the formulas (I) and (IIa) and (IIIa):

(I)
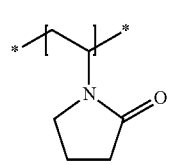

(IIa)
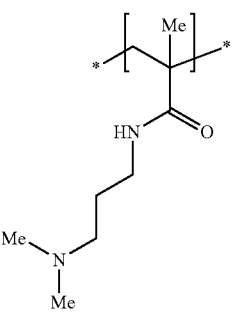

(IIIa)
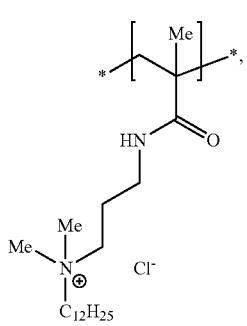

b) in particular from about 1.2 to about 3.2% by weight of at least one copolymer B, consisting of structural units of formulas (IVa) and/or (IVb) and (Va) and/or (Vb) and (VIa):

(IVa)
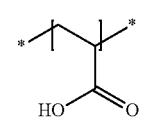

(IVb)
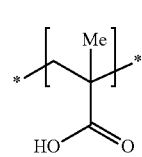

-continued

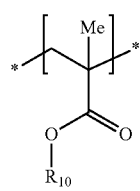

(Va)

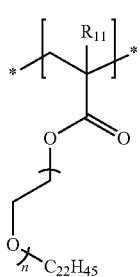

(Vb)

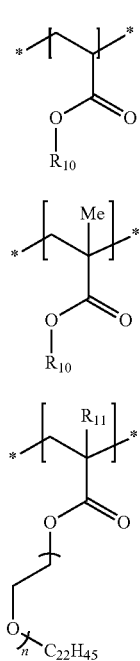

(VIa)

where
R$_{10}$ stands for a C$_{1-6}$ alkyl group,
R$_{11}$ stands for hydrogen or a methyl group, and
n stands for integers from about 22 to about 26,
c) from about 0.05 to about 7.0% by weight, preferably from about 0.1 to about 5.0% by weight, especially from about 0.1 to about 4.0% by weight, in particular from about 0.1 to about 3.0% by weight of at least one alkaline compound c) in the form of 2-amino-2-methylpropan-1-ol,
d) 0 to about 10% by weight, preferably from about 2.0 to about 8.5% by weight, in particular from about 3.0 to about 7.0% by weight of at least one vinyl pyrrolidone polymer and/or vinyl pyrrolidone/vinyl acetate copolymer and
e) 0 to about 3% by weight, preferably from about 0.05 to about 1.5% by weight, in particular from about 0.2 to about 0.8% by weight of a homopolyacrylic acid.

The aforementioned especially preferred embodiments (A)-(G) of the cosmetic agents as contemplated herein are exemplified by an excellent moisture resistance and by a good long-term hold. In addition, the polymer films formed from the aforementioned polymer combinations have enough flexibility, so that the formation of film plaques is prevented. Furthermore, these agents are exemplified by a stable viscosity and a high transparency.

In addition to the components described above, the cosmetic agents as contemplated herein may also contain additional ingredients. The group of these additional ingredients includes in particular the cosmetically active additives and auxiliary substances, in particular additional care substances.

The care substances used may include for example as silicone oil and/or a silicone gum. Suitable silicone oils or silicone gums as contemplated herein include in particular dialkylsiloxanes and alkylarylsiloxanes, such as, for example, dimethyl polysiloxane and methyl phenyl polysiloxane as well as their alkoxylated, quaternized or also anionic derivatives. Preferred examples include cyclic and linear polydialkylsiloxanes, their alkoxylated and/or aminated derivatives, dihydroxypolydimethylsiloxanes and polyphenylalkylsiloxanes in particular PEG-12 dimethicone and PEG-14 dimethicone.

The cosmetic agent as contemplated herein may additionally contain, for example, at least one protein hydrolysate and/or one of its derivatives as a care substance of another class of compounds. Protein hydrolysates are product mixtures obtained by acid, base or enzymatically catalyzed degradation of proteins. The term "protein hydrolysates" is also understood as contemplated herein to refer to total hydrolysates of individual amino acids and their derivatives as well as mixtures of various amino acids. The molecular weight of the protein hydrolysates that can be used as contemplated herein is between about 75, the molecular weight for glycine, and about 200,000 Dalton, but the molecular weight is from about 75 to about 50,000 Dalton, in particular from about 75 to about 20,000 Dalton.

The cosmetic agent as contemplated herein may additionally contain at least one vitamin, provitamins, vitamin precursor and/or derivatives thereof as the care substance. As contemplated herein, the preferred vitamins, provitamins and vitamin precursors are those which are usually assigned to the groups A, B, C, E, F and H.

The addition of panthenol can improve the flexibility of the polymer film formed by using the cosmetic agent as contemplated herein.

The cosmetic agents as contemplated herein may additionally contain at least one plant extract plus also monosaccharides and oligosaccharides and/or lipids as the care sub stance.

In addition, oil substances are also suitable as the care substance. The natural and synthetic cosmetic oil substances include, for example, vegetable oils, liquid paraffin oils, isoparaffin oils and synthetic hydrocarbons as well as di-n-alkyl ethers with a total of between 12 and 36 carbon atoms, in particular 12 to 24 carbon atoms.

Ester oils, i.e., the esters of C$_6$-C$_{30}$ fatty acids with C$_2$-C$_{30}$ fatty alcohols, preferably monoesters of fatty acids with alcohols with 2 to 24 carbon atoms, such as, for example, isopropyl myristate (Rilanit® IPM), isononanoic acid C$_{16-18}$ alkyl esters (Cetiol® SN), 2-ethylhexyl palmitate (Cegesoft® 24), steric acid 2-ethylhexy ester (Cetiol® 868), cetyl oleate, glycerin tricaprylate, coco fatty alcohol caprinate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V) are additional preferred substances for use as care additives.

Suitable care substances also include dicarboxylic acid esters, symmetrical, asymmetrical or cyclic esters of carbonic acids with fatty alcohols, trifatty acid esters of saturated and/or unsaturated linear and/or branched fatty acids with glycerin or fatty acid partial glycerides, including monoglycerides, diglycerides and their technical-grade mixtures.

In addition, the cosmetic agents as contemplated herein preferably contain emulsifiers and/or surface-active agents. Preferred PEG derivatives of hydrogenated castor oil are available, for example, under the brand name PEG hydrogenated castor oil, e.g., PEG-30 hydrogenated castor oil, PEG-33 hydrogenated castor oil, PEG-35 hydrogenated castor oil, PEG-36 hydrogenated castor oil or PEG-40 hydrogenated castor oil. The use of PEG-40 hydrogenated castor oil is preferred as contemplated herein. These oils are preferably present in a total amount of from about 0.05% to about 1.5% by weight, preferably from about 0.1% to about 1.0% by weight, especially from about 0.2% to about 0.8% by weight, in particular from about 0.3% to about 0.6% by weight, based on the total weight of the cosmetic agent.

The cosmetic agents as contemplated herein may be finished in the usual forms used for temporary shaping of keratinic fibers, in particular hair, for example, as a hair gel, hair spray, hair foam or hair wax. Finishing as a hair gel is preferred.

Both hair foams and hair sprays require the presence of blowing agents and are fabricated as so-called aerosols. Vessels made of metal (aluminum), tin plate (tin), protected and/or shatterproof plastics or glass coated with plastic on the outside may be used as the pressure-resistant containers, wherein the choice of the metal or other materials is based on compressive strength and fracture strength, corrosion resistance, ease of filling as well as aesthetic factors, ease of handling, printability, etc., all of which play a role. Special protective interior paints ensure corrosion resistance with respect to the cosmetic agents as contemplated herein in the pressurized container. The valves that are used especially preferably have a valve plate that is painted on the interior, wherein the painting and the valve material are compatible with one another. If aluminum valves are used, then their valve plates may be coated on the inside with Microflex paint, for example. If tin-plate valves are used as contemplated herein, their valve plates may be coated on the inside with PET (polyethylene terephthalate), for example. With a given spray apparatus, the sizes of the aerosol droplets and the respective size distribution can be adjusted on the basis of the quantity ratio of the blowing agent to the other components of the cosmetic agents.

If the cosmetic agent contains a blowing agent, then it is advantageously present in a total amount of from about 10% to about 80% by weight, preferably from about 20% to about 70% by weight, in particular from about 30% to about 60% by weight, based on the total weight of the cosmetic agent.

Blowing agents suitable as contemplated herein are selected from $N_2O$, dimethyl ether, $CO_2$, air, alkanes with 3 to 5 carbon atoms such as propane, n-butane, isobutane, n-pentane and isopentane, as well as mixtures thereof, for example. Dimethyl ether, propane, n-butane, isobutane and mixtures thereof are preferred. According to a preferred embodiment, the aforementioned alkanes, mixtures of the aforementioned alkanes or mixtures of the aforementioned alkanes with dimethyl ether may be used as the only blowing agent. However, the present disclosure explicitly also includes the joint use of blowing agents of the fluorochlorocarbon type, in particular the fluorocarbon type.

Most especially preferred are dimethyl ethers or mixtures of propane and butane as the sole blowing agent in a weight ratio of propane to butane of from about 20:80 to about 15:85. The mixtures are in turn preferably used in the agents as contemplated herein in a total amount of from about 30% to about 55% by weight, based on the total weight of the cosmetic agent. As contemplated herein, the term "butane" is understood to refer to n-butane, isobutane as well as mixtures of n-butane and isobutane.

Another subject matter of the present disclosure is a method for temporary shaping of keratinic fibers, wherein a cosmetic agent as contemplated herein is applied to the keratinic fibers and the latter are then brought to the desired shape.

With respect to additional preferred embodiments of the method as contemplated herein, what was said regarding the cosmetic agents as contemplated herein above also applies here, mutatis mutandis.

Furthermore, another subject matter of the present disclosure is the use of a cosmetic agent as contemplated herein for temporary shaping of keratinic fibers.

Finally, another subject matter of the present disclosure is the use of a cosmetic agent as contemplated herein to improve the moisture resistance of temporarily shaped keratinic fibers.

With respect to additional preferred embodiments of the uses as contemplated herein, what was also said above about the cosmetic agents as contemplated herein and the methods as contemplated herein also applies here, mutatis mutandis.

The present disclosure is described briefly by the following points in particular:

1. A cosmetic agent for temporary shaping of keratinic fibers, containing in a cosmetically tolerable vehicle:

a) at least one copolymer A, comprising at least one structural unit of formula (I) and at least one structural unit of formula (II) and at least one structural unit of formula (III):

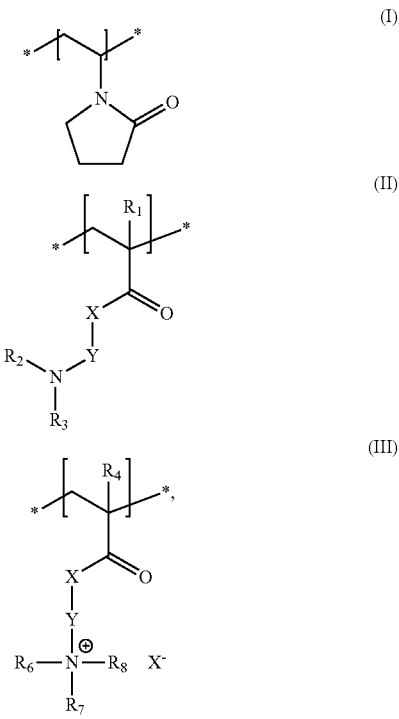

where $R_1$ and $R_4$ each independently of one another stand for hydrogen or a $C_{1-4}$ alkyl group, X stands for oxygen or an NH group, Y stands for a $C_{2-10}$ alkyl group, $R_2$, $R_3$, $R_6$, $R_8$ each independently of one another stand for a $C_{1-8}$ alkyl group, $R_7$ stands for a linear or branched, saturated or unsaturated $C_{6-30}$ alkyl group and $X^-$ stands for a physically tolerable anion, in particular chloride, b) at least one copolymer B comprising at least one structural unit of formula (IV) and at least one structural unit of formula (V) and at least one structural unit of formula (VI):

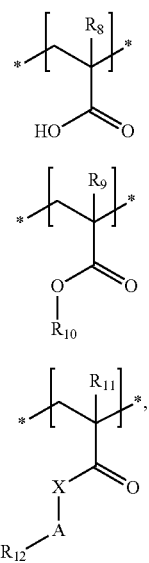

(IV), (V), (VI)

where $R_8$, $R_9$ and $R_{11}$ each independently of one another, stand for hydrogen or a $C_{1-4}$ alkyl group, $R_{10}$ stands for a $C_{1-6}$ alkyl group, X stands for oxygen or an NH group, A stands for a group *—$(CH_2CH_2O)_n$—* or for a group *—$(CH_2CHMeO)_m$—* or for a group *—$(CH_2CH_2O)_n$—$(CH_2CHMeO)_m$—* where n and m, each independently of one another, stand for integers from 5 to 35, $R_{12}$ stands for a linear or branched, saturated or unsaturated $C_{8-30}$ alkyl group, and c) at least one alkaline compound.

2. The cosmetic agent according to point 1, exemplified in that copolymer A contains from about 55 to about 68% by weight, preferably from about 62 to about 68% by weight structural units of formula (I), from about 5 to about 15% by weight, preferably from about 7 to about 9% by weight structural units of formula (II) and from about 25 to about 35% by weight, preferably from about 27 to about 31% by weight structural units of formula (III), based on the total weight of copolymer A.

3. The cosmetic agent according to any one of points 1 or 2, exemplified in that the radicals $R_1$ and $R_4$ each independently of one other in the structural units of formulas (II) and (III) stand for a hydrogen atom or a methyl group.

4. The cosmetic agent according to any one of the preceding points, exemplified in that the radicals $R_2$, $R_3$, $R_6$ and $R_8$ each independently of one other in the structural units of formulas (II) and (III) stand for a methyl group.

5. The cosmetic agent according to any one of the preceding points, exemplified in that in the structural units of formulas (II) and (III), X stands for an NH group and Y stands for a $C_{2-8}$ alkyl group, preferably a $C_{2-6}$ alkyl group, in particular a $C_3$ alkyl group.

6. The cosmetic agent according to any one of the preceding points, exemplified in that in the structural unit of formula (III) the radical $R_7$ stands for a linear or branched, saturated or unsaturated $C_{8-25}$ alkyl group, preferably a linear or branched, saturated or unsaturated $C_{8-20}$ alkyl group, especially a linear or branched, saturated or unsaturated $C_{8-15}$ alkyl group, in particular a linear or branched, saturated or unsaturated $C_{8-12}$ alkyl group.

7. The cosmetic agent according any one of the preceding points, exemplified in that the copolymer A contains at least one structural unit of formula (I) and at least one structural unit of formula (IIa) and at least one structural unit of formula (IIIa):

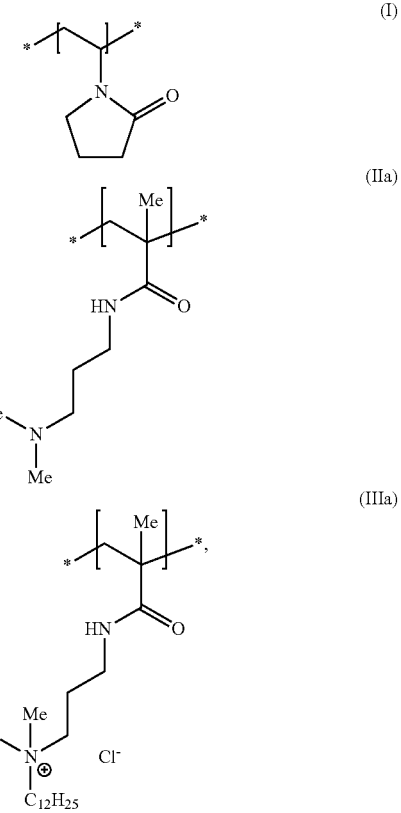

8. The cosmetic agent according to point 7, exemplified in that the copolymer A consists of structural units of formulas (I), (IIa) and (IIIa).

9. The cosmetic agent according to any one of the preceding points, exemplified in that the at least one copolymer A is present in a total amount of from about 0.01 to about 5.0% by weight, preferably from about 0.05 to about 4.0% by weight, especially from about 0.1 to about 3.0% by weight, in particular from about 0.2 to about 1.5% by weight, based on the total weight of the cosmetic agent.

10. The cosmetic agent according to any one of the preceding points, exemplified in that the radicals $R_8$, $R_9$ and $R_{11}$ each independently of one another in the structural units of formulas (IV), (V) and (VI) stand for hydrogen or a methyl group.

11. The cosmetic agent according to any one of the preceding points, exemplified in that in the structural unit of formula (VI), X stands for an oxygen atom and A stands for a group *—$(CH_2CH_2O)_n$—*, where n denotes integers from 10 to 30, in particular from 20 to 30.

12. The cosmetic agent according to any one of the preceding points, exemplified in that in the structural units of formula (III) the radical $R_{12}$ stands for a linear or branched, saturated or unsaturated $C_{10-25}$ alkyl group, preferably for a linear or branched, saturated or unsaturated $C_{12-26}$ alkyl group, especially for a linear or branched, saturated or unsaturated $C_{16-24}$ alkyl group, in particular for a linear or branched, saturated or unsaturated $C_{20-24}$ alkyl group.

13. The cosmetic agent according to any one of the preceding points, exemplified in that the copolymer B comprises at least one structural unit of formula (IVa) and at least one structural unit of formula (IVb) and at least one structural unit of formula (Va) and at least one structural unit of formula (Vb) and at least one structural unit of formula (VIa):

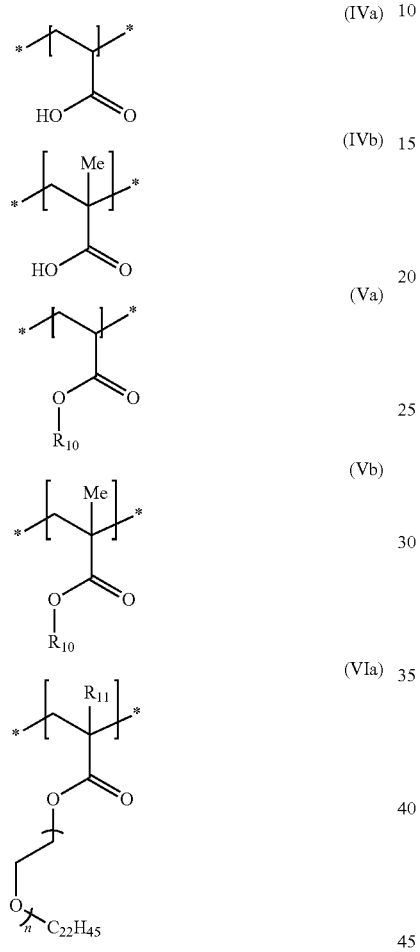

where
R$_{10}$ stands for a C$_{1-6}$ alkyl group,
R$_{11}$ stands for hydrogen or a methyl group and
n stands for integers from 22 to 26.

14. The cosmetic agent according to point 13, exemplified in that copolymer B consists of structural unit of formulas (IVa) and/or (IVb) and (Va) and/or (Vb) and (VIa).

15. The cosmetic agent according to any one of the preceding points, exemplified in that the at least one copolymer B is present in a total amount of from about 0.01 to about 5.0% by weight, preferably from about 0.05 to about 4.0% by weight, especially from about 0.1 to about 3.0% by weight, in particular from about 0.2 to about 1.5% by weight, based on the total weight of the cosmetic agent.

16. The cosmetic agent according to any one of the preceding points, exemplified in that the cosmetic agent has a weight ratio of the total amount of the at least one copolymer A to the total amount of the at least one copolymer B of from about 25:1 to about 1:20, preferably from about 10:1 to about 1:10, especially from about 4:1 to about 1:3, in particular from about 2:1 to about 1:2.

17. The cosmetic agent according to any one of the preceding points, exemplified in that the alkaline compound c) is selected from the group of 2-aminoethan-1-ol (monoethanolamine), tris(2-hydroxyethyl)amine (triethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 2-amino-2-methylpropan-1-ol, 1-amino-2-methylpropan-2-ol, 3-aminopropane-1,2-diol, 2-amino-2-methylpropane-1,3-diol, in particular 2-amino-2-methylpropan-1-ol.

18. The cosmetic agent according to any one of the preceding points, exemplified in that the alkaline compound c) is present in a total amount of from about 0.05 to about 7.0% by weight, preferably from about 0.1 to about 5.0% by weight, especially from about 0.1 to about 4.0% by weight, in particular from about 0.1 to about 3.0% by weight, based on the total amount of the cosmetic agent.

19. The cosmetic agent according to any one of the preceding points, exemplified in that the cosmetic agent additionally contains at least one additional film-forming and/or hair setting polymer which is different from copolymer A and copolymer B.

20. A method for temporary shaping of keratinic fibers, wherein a cosmetic agent according to any one of points 1 to 19 is applied to the keratinic fibers and these fibers are then brought into the desired shape.

21. A use of a cosmetic agent according to any one of points 1 to 19 for temporary shaping of keratinic fibers.

22. The use of a cosmetic agent according to any one of points 1 to 19 to improve the moisture resistance of temporarily shaped keratinic fibers.

The following examples illustrate the present disclosure but without restricting it:

EXAMPLES

1. Formulations (All Amounts in % by Weight, Based on the Total Weight of the Respective Cosmetic Agent):

| Raw material | V1 | V2 | E1 |
|---|---|---|---|
| Styleze W 20 (copolymer A) [1)] | 8.4 | — | 4.2 |
| Aculyn 28 (copolymer B) [2)] | — | 8.4 | 4.2 |
| AMP-Ultra PC 2000 (alkaline compound) [3)] | 0.18 | 0.12 | 0.30 |
| Water | to Σ 100 | to Σ 100 | to Σ 100 |

[1)] INCI designation: polyquaternium-55 (19-21% by weight dispersion, ISP)
[2)] INCI designation: acrylates/beheneth-25 methacrylate copolymer (19-21% by weight dispersion in water, Rohm & Haas)

Cosmetic agents V1, V2 and E1 were obtained by combining the above ingredients. The polymer content in the cosmetic agents V1, V2 and E1 amounts to 0.8% by weight in each case.

The cosmetic agents thereby produced were tested for their moisture resistance by employing the HHCR test (high humidity curl retention test).

To do so, 10 strands of hair (European natural, type 827560 bound at one end, not glued, color 6/0, length 240 mm, weight ~0.6 g, L$_{max}$=220 mm, Kerling Internationale Haarfarbrik GmbH) were prepared for each cosmetic agent V1, V2 and E1 by applying 180 mg of the respective cosmetic agent to the strands of hair and massaging it in by hand. Next the strands of hair were wound onto rollers (length 160 mm, diameter 10 mm) and dried overnight at 298 K and 50% relative atmospheric humidity. After unrolling the strands of hair, they were attached to a metal frame, placed in a climate chamber at 298 K and 85% relative atmospheric humidity and their length was determined by employing a laser immediately thereafter (corresponds to the value Lo). After another 6 hours, the length of the hair strands was determined again (corresponds to the value $L_1$).

The moisture resistance, i.e., the HHCR value, is calculated according to the following equation using the values thereby determined:

$$HHCR = \frac{L_{max} - L_1}{L_{max} - L_0} * 100$$

The results were tested by the Mann Whitney U-test and were significant

The following table shows the HHCR values for the cosmetic agents V1, V2 and E1, where the expected value E(V1+V2) corresponds to the average of the HHCR values of the two individual copolymers A and B.

|  | V1 | V2 | E(V1 + V2) | E1 |
|---|---|---|---|---|
| HHCR (%) | 64 | 73 | 69 | 80 |

The HHCR value (cosmetic agent E1) determined for the combination as contemplated herein is thus significantly higher than the HHCR value to be expected for this combination (E(V1+V2)). A synergistic increase in the moisture resistance of cosmetic agents for temporary shaping of keratinic fibers in particular human hair is achieved by using the combination as contemplated herein of a copolymer A based on polyvinyl pyrrolidone with a copolymer B based on acrylates.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic agent for temporary shaping of keratinic fibers, comprising in a cosmetically tolerable vehicle:
   a) at least one copolymer A, consisting of at least one structural unit of formula (I) and at least one structural unit of formula (II) and at least one structural unit of formula (III):

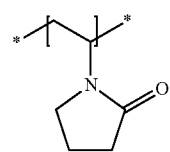
(I)

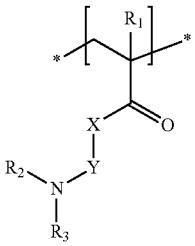
(II)

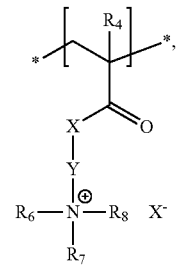
(III)

where
$R_1$ and $R_4$ each independently of one another stand for hydrogen or a $C_{1-4}$ alkyl group,
X stands for oxygen or an NH group,
Y stands for a $C_{2-10}$ alkyl group,
$R_2$, $R_3$, $R_6$, $R_8$ each independently of one another stand for a $C_{1-8}$ alkyl group,
$R_7$ stands for a linear or branched, saturated or unsaturated $C_{6-30}$ alkyl group and
$X^-$ stands for a physically tolerable anion,
   b) at least one copolymer B comprising at least one structural unit of formula (IV) and at least one structural unit of formula (V) and at least one structural unit of formula (VI):

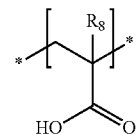
(IV)

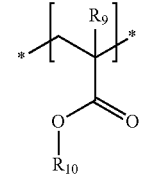
(V)

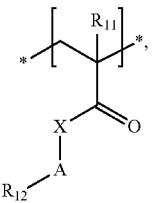
(VI)

where
$R_8$, $R_9$ and $R_{11}$ each independently of one another, stand for hydrogen or a $C_{1-4}$ alkyl group,
$R_{10}$ stands for a $C_{1-6}$ alkyl group, X stands for oxygen or an NH group, A stands for a group *—(CH$_2$CH$_2$O)$_n$—* or for a group *—(CH$_2$CHMeO)$_m$—* or for a group *—(CH$_2$CH$_2$O)$_n$—(CH$_2$CHMeO)$_m$—* where n and m, each independently of one another, stand for integers from 5 to 35, R$_{12}$ stands for a linear or branched, saturated or unsaturated C$_{8-30}$ alkyl group, and c) at least one alkaline compound.

2. The cosmetic agent according to claim 1, wherein the copolymer A consists of at least one structural unit of formula (I) and at least one structural unit of formula (IIa) and at least one structural unit of formula (IIIa):

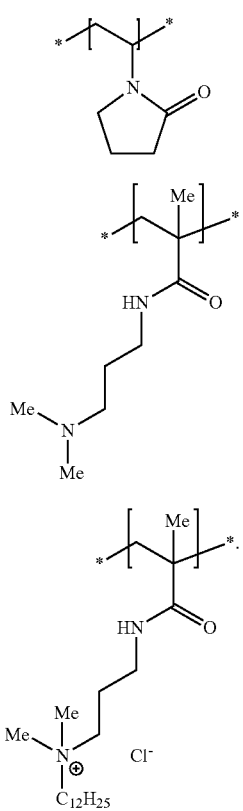

3. The cosmetic agent according to claim 1, wherein copolymer B comprises at least one structural unit of formula (IVa) and at least one structural unit of formula (IVb) and at least one structural unit of formula (Va) and at least one structural unit of formula (Vb) and at least one structural unit of formula (VIa):

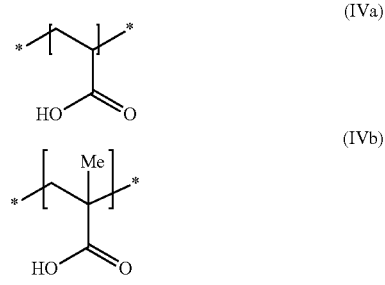

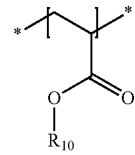

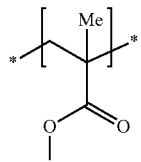

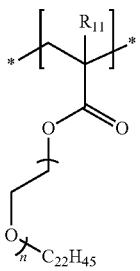

where

R$_{10}$ stands for a C$_{1-6}$ alkyl group,

R$_{11}$ stands for hydrogen or a methyl group and n stands for integers from 22 to 26.

4. The cosmetic agent according to claim 1, wherein the at least one copolymer B is present in a total amount of from about 0.01 to about 5.0% by weight, based on the total weight of the cosmetic agent.

5. The cosmetic agent according to claim 1, wherein the cosmetic agent has a weight ratio of the total amount of the at least one copolymer A to the total amount of the at least one copolymer B of from about 25:1 to about 1:20.

6. The cosmetic agent according to claim 1, wherein the alkaline compound c) is selected from the group of 2-aminoethan-1-ol (monoethanolamine), tris(2-hydroxyethyl)amine (triethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 2-amino-2-methylpropan-1-ol, 1-amino-2-methylpropan-2-ol, 3-aminopropane-1,2-diol, 2-amino-2-methylpropane-1,3-diol, and combinations thereof.

7. The cosmetic agent according to claim 1, wherein the alkaline compound c) is present in a total amount of from about 0.05 to about 7.0% by weight, based on the total amount of the cosmetic agent.

8. A method for temporary shaping of keratinic fibers, the method comprising:

applying to the keratinic fibers a cosmetic agent comprising in a cosmetically tolerable vehicle:

a) at least one copolymer A, consisting of at least one structural unit of formula (I) and at least one structural unit of formula (II) and at least one structural unit of formula (III):

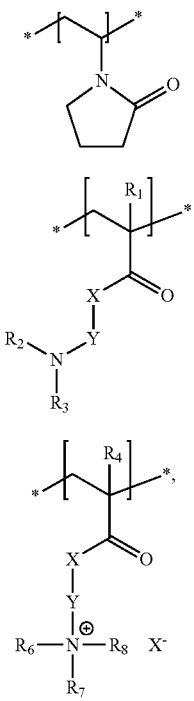

(I), (II), (III)

where
R₁ and R₄ each independently of one another stand for hydrogen or a $C_{1-4}$ alkyl group,
X stands for oxygen or an NH group,
Y stands for a $C_{2-10}$ alkyl group,
R₂, R₃, R₆, R₈ each independently of one another stand for a $C_{1-8}$ alkyl group,
R₇ stands for a linear or branched, saturated or unsaturated $C_{6-30}$ alkyl group and
X⁻ stands for a physically tolerable anion,
b) at least one copolymer B comprising at least one structural unit of formula (IV) and at least one structural unit of formula (V) and at least one structural unit of formula (VI):

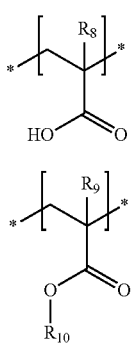

(IV), (V)

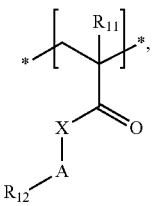

(VI)

where
R₈, R₉ and R₁₁ each independently of one another, stand for hydrogen or a $C_{1-4}$ alkyl group,
R₁₀ stands for a $C_{1-6}$ alkyl group,
X stands for oxygen or an NH group,
A stands for a group *—$(CH_2CH_2O)_n$—* or for a group *—$(CH_2CHMeO)_m$—* or for a group *—$(CH_2CH_2O)_n$—$(CH_2CHMeO)_m$—* where n and m, each independently of one another, stand for integers from 5 to 35,
R₁₂ stands for a linear or branched, saturated or unsaturated $C_{8-30}$ alkyl group, and
c) at least one alkaline compound; and
bringing the keratinic fibers into the desired shape.

9. The cosmetic agent according to claim 1, wherein the radicals R₁ and R₄ each independently of one other in the structural units of formulas (II) and (III) stand for a hydrogen atom or a methyl group.

10. The cosmetic agent according to claim 1, wherein the radicals R₂, R₃, R₆ and R₈ each independently of one other in the structural units of formulas (II) and (III) stand for a methyl group.

11. The cosmetic agent according to claim 1, wherein in the structural units of formulas (II) and (III), X stands for an NH group and Y stands for a $C_{2-6}$ alkyl group.

12. The cosmetic agent according to claim 1, wherein in the structural unit of formula (III) the radical R₇ stands for a linear or branched, saturated or unsaturated $C_{8-12}$ alkyl group.

13. The cosmetic agent according to claim 1, wherein the at least one copolymer A is present in a total amount of from about 0.01 to about 5.0% by weight, based on the total weight of the cosmetic agent.

14. The cosmetic agent according to claim 1, wherein the radicals R₈, R₉ and R₁₁ each independently of one another in the structural units of formulas (IV), (V) and (VI) stand for hydrogen or a methyl group.

15. The cosmetic agent according to claim 1, wherein in the structural unit of formula (VI), X stands for an oxygen atom and A stands for a group *—$(CH_2CH_2O)_n$—*, where n denotes integers from about 10 to about 30.

16. The cosmetic agent according to claim 1, wherein in the structural units of formula (III) the radical R₁₂ stands for a linear or branched, saturated or unsaturated $C_{20-24}$ alkyl group.

17. The cosmetic agent according to claim 1, wherein the alkaline compound c) is 2-amino-2-methylpropan-1-ol.

\* \* \* \* \*